United States Patent
Cui et al.

(10) Patent No.: US 11,242,268 B2
(45) Date of Patent: *Feb. 8, 2022

(54) COMPOUND HEAVY METAL CHELATING AGENT CONTAINING DITHIOCARBOXYLATE FUNCTIONALIZED ETHOXYLATED PENTAERYTHRITOL CORE HYPERBRANCHED POLYMER

(71) Applicants: Shandong Xintai Water Treatment Technology Co., Ltd., Shandong (CN); Tongji University, Shanghai (CN)

(72) Inventors: Jin Cui, Shandong (CN); Bingru Zhang, Shanghai (CN); Fengting Li, Shanghai (CN)

(73) Assignees: Shandong Xintai Water Treatment Technology Co., Ltd., Shandong (CN); Tongji University, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/994,677

(22) Filed: Aug. 17, 2020

(65) Prior Publication Data
US 2020/0377391 A1     Dec. 3, 2020

(30) Foreign Application Priority Data
Dec. 2, 2019  (CN) .......................... 201911215692.0

(51) Int. Cl.
*C02F 1/62* (2006.01)
*C07C 333/16* (2006.01)
*C02F 1/54* (2006.01)
*C02F 101/20* (2006.01)

(52) U.S. Cl.
CPC .................. *C02F 1/62* (2013.01); *C02F 1/54* (2013.01); *C07C 333/16* (2013.01); *C02F 2101/20* (2013.01)

(58) Field of Classification Search
CPC ......................................................... C02F 1/62
USPC .......................................... 510/446; 210/688
See application file for complete search history.

(56) References Cited

U.S. PATENT DOCUMENTS

| | | | | |
|---|---|---|---|---|
| 8,211,389 B2* | 7/2012 | Zinn | ......................... | C02F 1/56 423/42 |
| 9,499,420 B2* | 11/2016 | Ross | ......................... | C02F 1/56 |
| 2008/0038169 A1* | 2/2008 | Phan | ......................... | C22B 3/44 423/120 |
| 2018/0215636 A1* | 8/2018 | Zhang | ................. | C08G 83/004 |

FOREIGN PATENT DOCUMENTS

JP     2008-18311 A  *  1/2008 ............... C02F 1/62

OTHER PUBLICATIONS

English Translation of JP2008-18311, Kobayshi et al. "Treating agent for heavy metal containing wastewater and method for wastewater treatment using the same" (Year: 2008).*

* cited by examiner

*Primary Examiner* — Nina Bhat

(57) ABSTRACT

A compound heavy metal chelating agent, which relates to the field of chemical and environmental protection technology, includes dithiocarboxylate functionalized ethoxylated pentaerythritol core hyperbranched polymer and alkylene diamine-N,N'-sodium bisdithiocarboxylate with a molar ratio in a range of 1:1.0 to 1:10.0. The two different structural types of components have the synergistic positive effect. While chelating heavy metals, the compound heavy metal chelating agent alternately combine with heavy metals to form insoluble chelating super-molecular deposits, which has both chelation and flocculation functions. The compound heavy metal chelating agent meets the standard for treating heavy metal wastewater, and low concentration heavy metal wastewater. It has a wide adaptability range, and does not need to add coagulant. Moreover, it is simple in preparation method, easily available for raw materials, low in cost, and easy to be industrialized.

6 Claims, No Drawings

COMPOUND HEAVY METAL CHELATING AGENT CONTAINING DITHIOCARBOXYLATE FUNCTIONALIZED ETHOXYLATED PENTAERYTHRITOL CORE HYPERBRANCHED POLYMER

CROSS REFERENCE OF RELATED APPLICATION

The present invention claims priority under 35 U.S.C. 119(a-d) to CN 201911215692.0, filed Dec. 2, 2019.

BACKGROUND OF THE PRESENT INVENTION

Field of Invention

The present invention relates to the field of chemical industry and environmental protection technology, and more particularly to a compound heavy metal chelating agent containing dithiocarboxylate functionalized ethoxylated pentaerythritol core hyperbranched polymer and its preparation methods and applications.

Description of Related Arts

In recent years, heavy metal pollution has become the main environmental crisis in China, posing a serious threat to the ecosystem and the health of the people. With the continuous upgrading of national environmental protection monitoring, the electroplating and steel industries began to implement special heavy metal emission limit standards in Table 3 of "Emission Standards of Electroplating Pollutant (GB21900-2008)" and "Emission Standards of Water Pollutants for Steel Industry (GB13456-2012)". Heavy metal emission indicators are more stringent, such as copper emission indicator decreases from 0.5 mg/L to 0.3 mg/L, nickel emission indicator for electroplating industry decreases from 0.5 mg/L to 0.1 mg/L, nickel emission indicator for steel industry is more stringent and decreases from 1.0 mg/L to 0.05 mg/L; other heavy metal emission indicators also decrease. Therefore, the effective heavy metal wastewater treatment technology has become an urgent need in the field of national economy and environmental protection.

Heavy metal wastewater treatment technologies include chemical precipitation method, adsorption method, ion exchange method, reverse osmosis method, and electrochemical method. The chemical precipitation method is simple, efficient and economical, and is suitable for the treatment of large-scale heavy metal wastewater. The adsorption method has problems of large amount of waste residues and difficult treatment of the residues; the ion exchange method, the reverse osmosis method, and the electrochemical method are high in investment and treatment costs, and are not suitable for the treatment of large amounts of heavy metal wastewater. Therefore, the chemical precipitation method is the main technology of heavy metal wastewater treatment.

The chemical precipitation method includes steps of adding a chemical precipitant to the heavy metal wastewater, and chemically reacting with the heavy metal to form an insoluble solid substance, and then performing solid-liquid separation to remove the heavy metal in the wastewater. Commonly used chemical agents are inorganic precipitants and organic chelating agents. Although inorganic precipitants (such as hydroxides and sulfides) are simple and low in cost, they have their inherent limitations: (1) a large amount of alkali is required to adjust the pH value; (2) they are easy to form colloids; (3) the precipitation is small, a large amount of flocculants need to be added, and the amount of heavy metal sludge is large; (4) complex heavy metal wastewater is unable to be treated; and (5) the residual heavy metal concentration is far from meeting the current emission standards.

The organic chelating agent has a dithiocarboxylic acid group ($CSS^-$, hereinafter referred to as DTC). Because the dithiocarboxylic acid group is able to form an insoluble solid with extremely low solubility and strong stability with heavy metals, it is increasingly used in heavy metal wastewater treatment. Compared with inorganic precipitants, organic chelating agents are able to directly deal with complex heavy metals, the pH adaptation range is broadened, heavy metal residues are low, and the sludge quantity is small.

Currently, there are three types of DTC organic chelating agents as follows.

(1) Single DTC small molecule organic chelating agent, which contains 1 DTC group in molecular structure, such as N,N-dimethyl dithiocarboxylate and N,N-diethyl dithiocarboxylate;

(2) Multi-DTC small molecule organic chelating agent, which contains more than 2 DTC groups in molecular structure, such as disodium N,N'-bis-(dithiocarboxy) ethylenediamine (disclosed by CN 101857296), disodium N,N'-bis-(dithiocarboxy) piperazine (disclosed by CN 102216410), and trisodium N,N',N''-tris-(dithiocarboxy) diethylenetriamine (disclosed by CN 1831020);

(3) Multi-DTC linear polymer chelating agent, in which multiple DTCs are grafted on the amino groups of linear polymers, such as polyethyleneimine (disclosed by CN 101081827), polyacrylamide (disclosed by CN 101979416) and starch (disclosed by CN 101759809).

For the single DTC small molecule organic chelating agent, the chelating ligand formed with heavy metals is small in molecular weight and light in density. It needs a large amount of flocculant to aid sedimentation, and is easy to re-dissolve and is difficult to stably meet the current emission standards. For multi-DTC small molecule organic chelating agent, it is usually that small molecule polyamino compound is grafted with multiple DTC groups, due to the small molecular structure, the DTC groups are completely exposed, thereby having high utilization efficiency; and however, the flocs are linear, the precipitation performance is unstable, the flocculant is still needed to aid sedimentation. For multi-DTC linear polymer chelating agent, there are multiple DTC groups on the linear molecular chain; after chelating with heavy metals, the multi-DTC linear polymer chelating agent is able to quickly flocculate to form large, fast-settling and easily separable deposits, it has good flocculation; and however, its linear molecular chain is easy to curl, and its DTC groups are unable not be completely exposed, so that steric hindrance is produced, thereby the utilization efficiency is low.

In recent years, compared with linear polymers, hyperbranched polymers, as a new class of three-dimensional polymers, have a precise molecular structure, a high degree of geometric symmetry, a large number of functional groups in the periphery, a cavity within the molecules and a controllable relative molecular mass, and their molecules have a nanometer size. A new class of DTC hyperbranched polymer-based heavy metal trapping agents is formed by grafting hyperbranched polymers containing terminal amine groups with DTC. The present inventor has disclosed a dithiocarboxylic acid functionalized dendritic hyperbranched polymer in CN 104326955, which takes trimethylolpropane as the core. The polymer has a three-dimensional spatial structure, and has both the high efficiency of DTC-based small-molecule heavy metal trapping agents and the flocculation of DTC-based linear polymer heavy metal trapping agents. Therefore, it has good application value.

The development of new heavy metal chelating agents with high chelating efficiency, good flocculation performance and low cost has always been the focus and difficulty of research by those skilled in the art.

SUMMARY OF THE PRESENT INVENTION

An object of the present invention is to provide a compound heavy metal chelating agent, which has high chelation efficiency, good flocculation settling effect and low cost.

To achieve the above object, the present invention provides a compound heavy metal chelating agent which comprises dithiocarboxylate functionalized ethoxylated pentaerythritol core hyperbranched polymer and alkylene diamine-N,N'-sodium bisdithiocarboxylate, wherein:

the dithiocarboxylate functionalized ethoxylated pentaerythritol core hyperbranched polymer has a chemical formula of $C[CH_2OCH_2CH_2OCOCH_2CH_2N(CSSM)(CH_2)_n NHCSSM]_4$, and a structural formula of

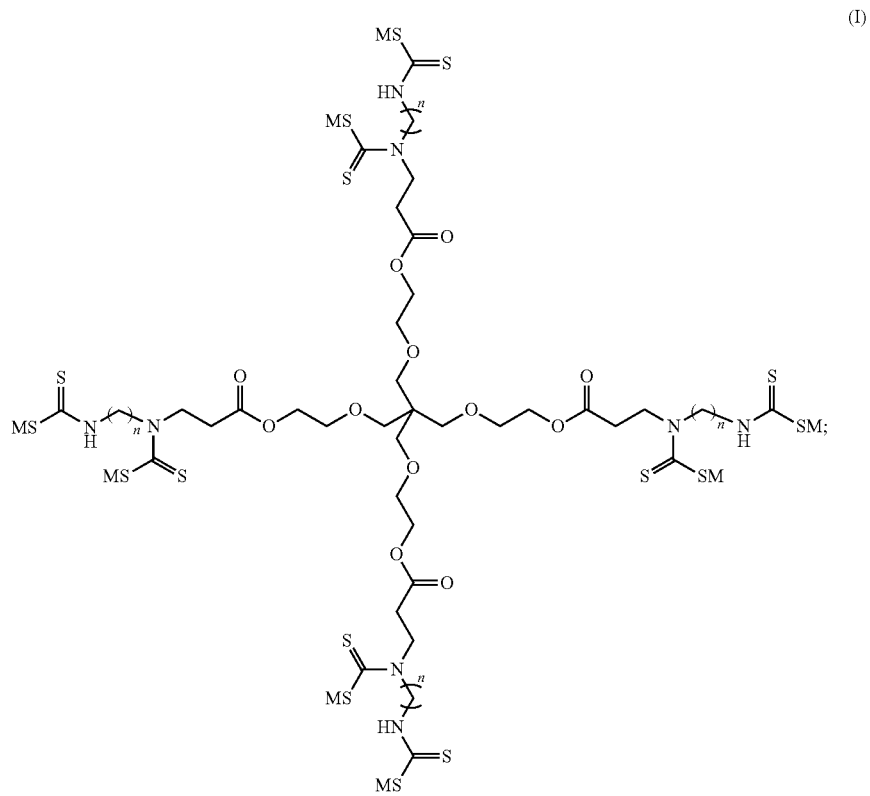

(I)

the alkylene diamine-N,N'-sodium bisdithiocarboxylate has a chemical formula of $(MSSC)_2N(CH_2)_nN(CSSM)_2$, and a structural formula of

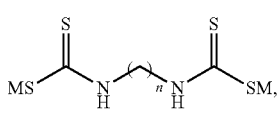

(II)

here n is a positive integer between 2 and 12, M is $Na^+$, $K^+$ or $NH_4^+$;

a molar ratio of the dithiocarboxylate functionalized ethoxylated pentaerythritol core hyperbranched polymer and the alkylene diamine-N,N'-sodium bisdithiocarboxylate is in a range from 1:1.0 to 1:10.0.

Also, the present invention provides a preparation method of the compound heavy metal chelating agent mentioned in the above technical solution, the preparation method comprising steps of:

(1) performing a first addition reaction, which comprises slowly adding a first low-carbon alcohol solution drop by drop into a second low-carbon alcohol solution at 20-25° C. under nitrogen protection, wherein the first low-carbon alcohol solution contains ethoxylated pentaerythritol tetraacrylate (EPTA) with a chemical formula of $C(CH_2OCH_2CH_2OCOCH=CH_2)_4$, the second low-carbon alcohol solution contains excessive alkylenediamine (ADA) with a chemical formula of $H_2N(CH_2)_nNH_2$, here n is a positive integer between 2 and 12; and then stirring for 20-48 h at 20-35° C., obtaining a mixed low-carbon alcohol solution which contains (N-(n-aminoalkylene))-3-aminopropionate hyperbranched polymer (EO-PETA/ADA) and unreacted alkylenediamine, wherein a reaction formula of the first addition reaction is expressed by a formula of (III)

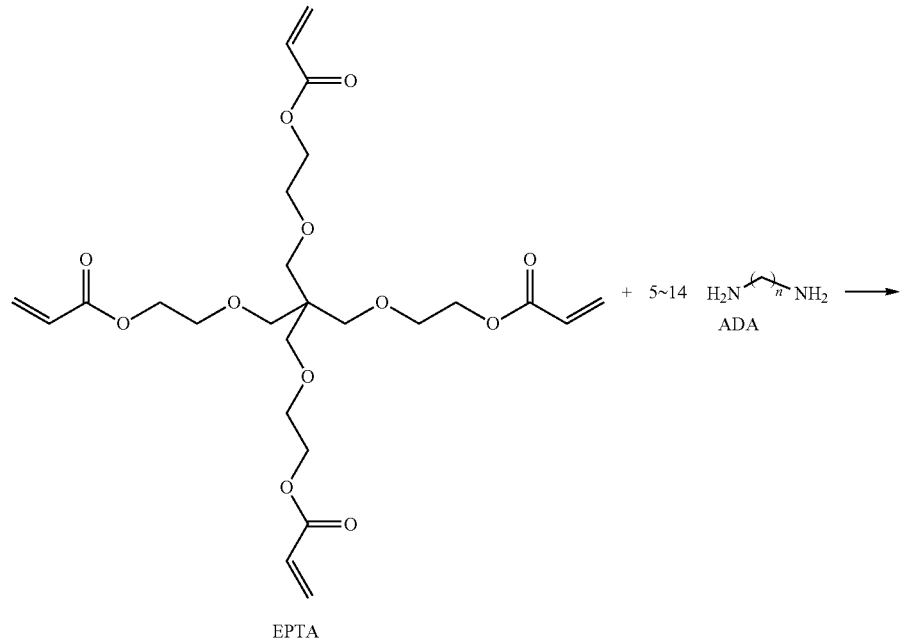

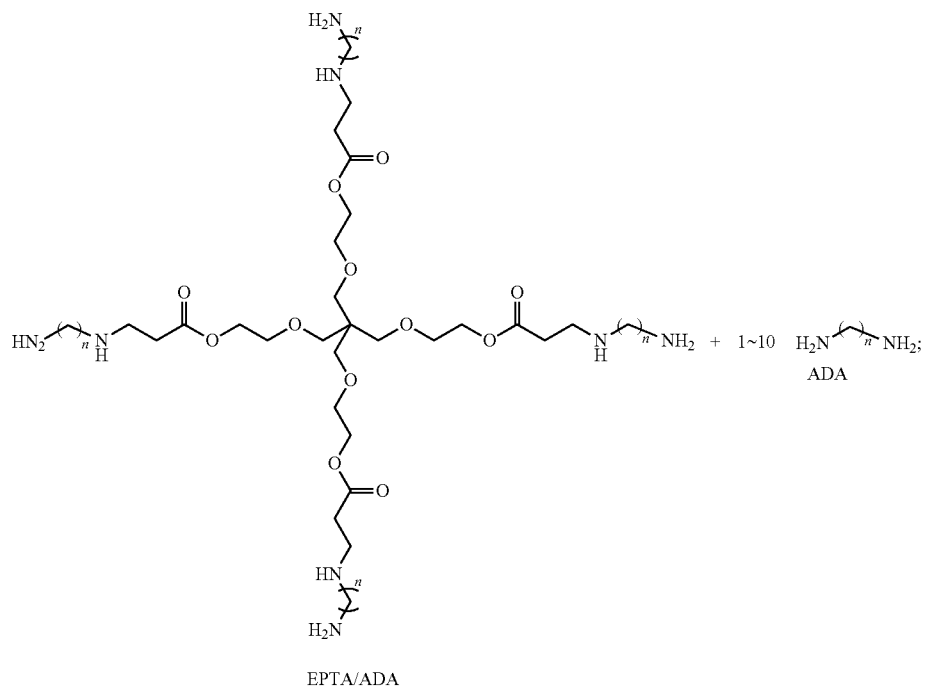

and (2) performing a second addition reaction, which comprises adding alkaline aqueous solution and carbon disulfide drop by drop after cooling the mixed low-carbon alcohol solution obtained by the step (1) to 10-25° C., stirring for 3-8 h at 20-35° C., standing at room temperature for 3-24 h, precipitating a solid product, filtering and drying to obtain the compound heavy metal chelating agent, wherein:

a molar ratio of the EPTA, the ADA, the alkali and the carbon di sulfide is in a range of 1:(5.0-14.0):(10.0-28.0):(10.0-28.0), and preferably, is in a range of 1:(8.0-12.0):(16.0-24.0):(16.0-24.0).

Preferably, a reaction formula of the second addition reaction is expressed by a formula of

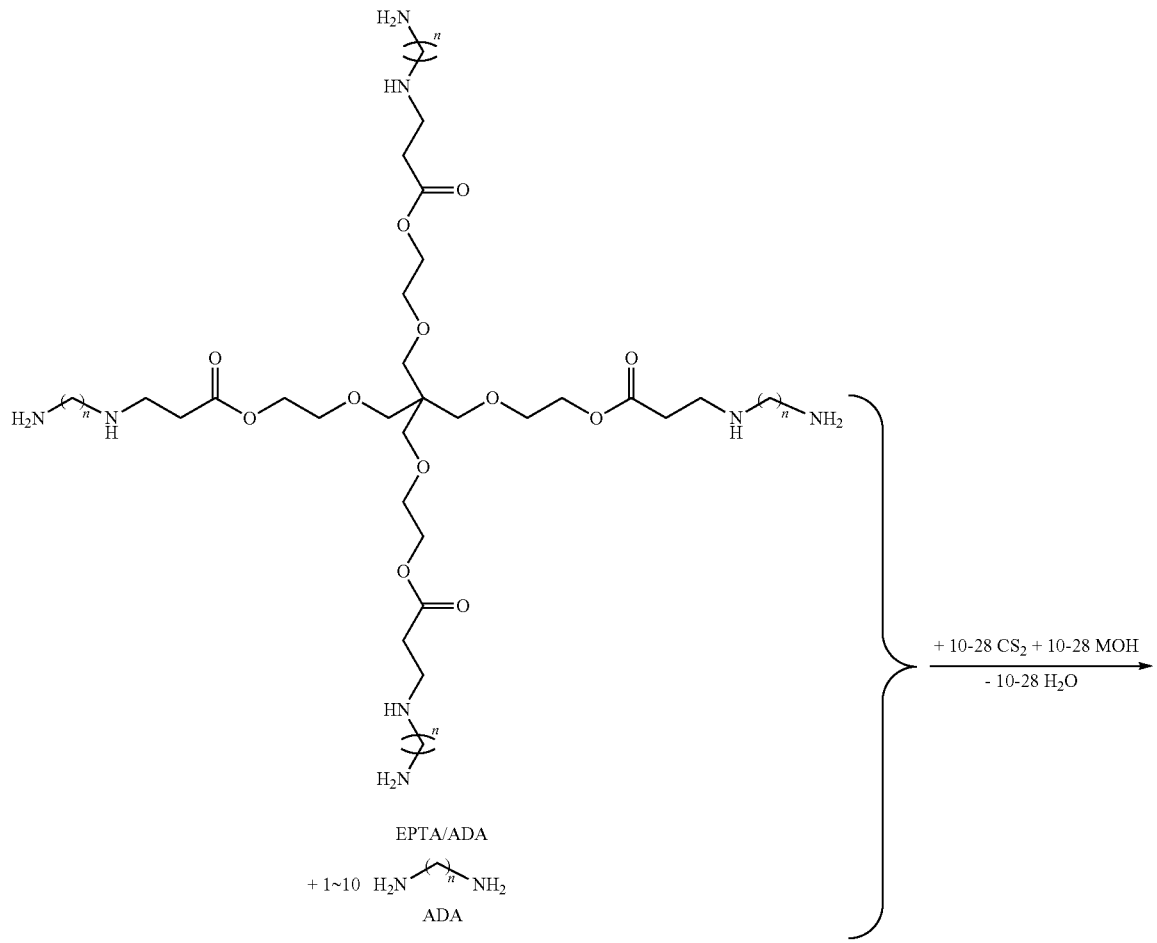

(IV)

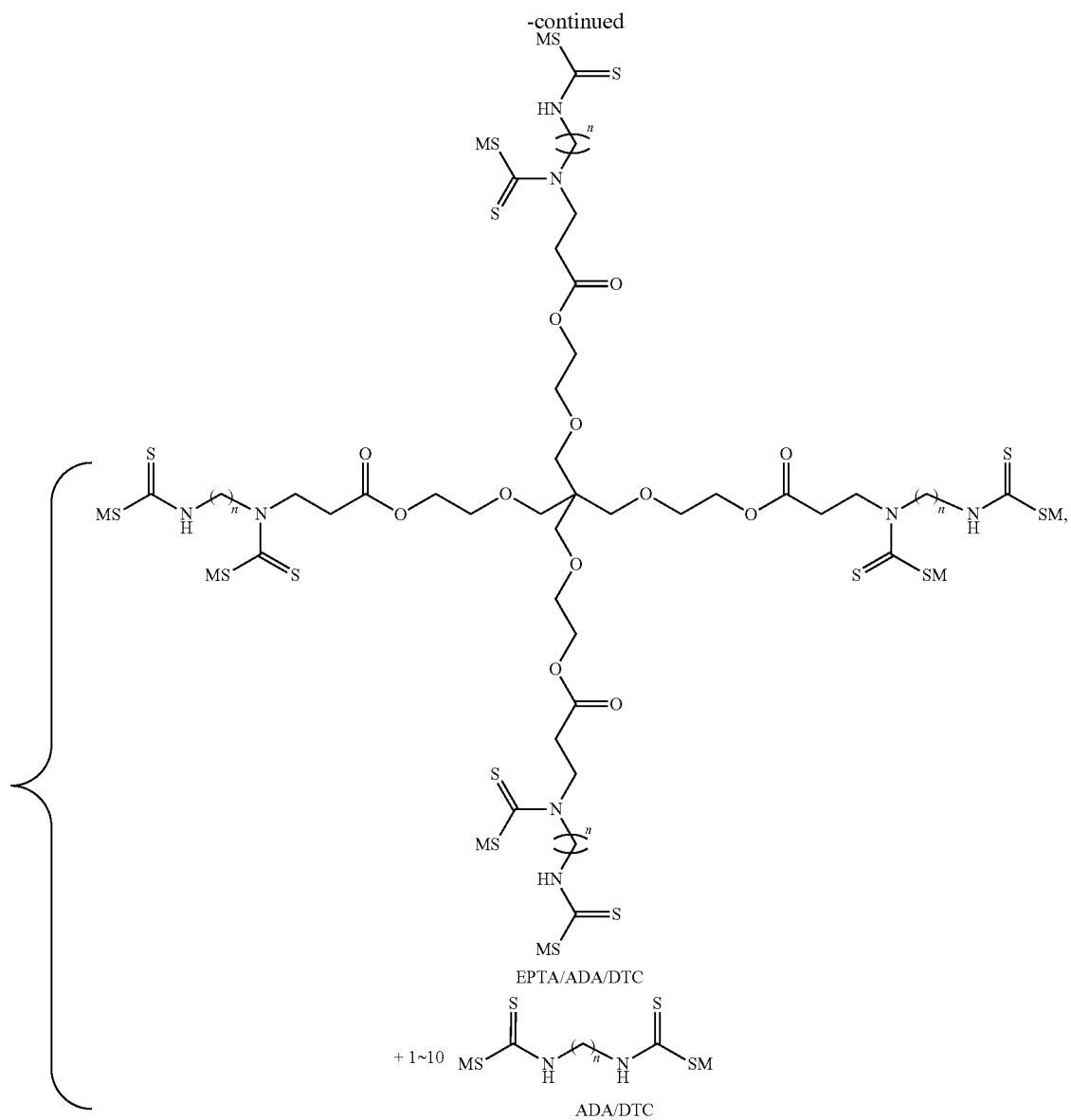

EPTA/ADA/DTC

ADA/DTC here, EPTA/ADA/DTC denotes the dithiocarboxylate functionalized ethoxylated pentaerythritol core hyperbranched polymer, ADA/DTC denotes alkylene diamine-N,N'-sodium bisdithiocarboxylate.

Preferably, each of the first low-carbon alcohol and the second low-carbon alcohol in the step (1) is one member selected from a group consisting of methanol, ethanol, propanol, ethylene glycol and propylene glycol.

Preferably, the first low-carbon alcohol solution containing ethoxylated pentaerythritol tetraacrylate is added drop by drop for 1-10 times, and more preferably, for 3-5 times, wherein after being added drop by drop every time, the first low-carbon alcohol solution is firstly stirred for 4-8 h, and then is added drop by drop for a next time.

Preferably, the alkali in the step (2) is one member selected from a group consisting of sodium hydroxide, potassium hydroxide and ammonia.

The compound heavy metal chelating agent provided by the present invention comprises the dithiocarboxylate functionalized ethoxylated pentaerythritol core hyperbranched polymer and the alkylene diamine-N,N'-sodium bisdithiocarboxylate, wherein due to special three-dimensional highly branched structure, the dithiocarboxylate functionalized ethoxylated pentaerythritol core hyperbranched polymer is able to effectively chelate heavy metals and compound with the alkylene diamine-N,N'-sodium bisdithiocarboxylate, thereby having a synergistic positive effect. Compared with similar drugs widely used in the market, the present invention is low in dosage. While chelating heavy metals, the dithiocarboxylate functionalized ethoxylated pentaerythritol core hyperbranched polymer forms a super-molecular chelate with the heavy metals. Therefore, the present invention has good flocculation settling performance.

The preparation method of the compound heavy metal chelating agent provided by the present invention is simple in process, easy to obtain raw materials, low in cost, and easy to be industrialized.

The present invention also provides an application of the compound heavy metal chelating agent mentioned above in the standard treatment of heavy metal wastewater.

The compound heavy metal chelating agent provided by the present invention is able to be used for heavy metal wastewater treatment in industries such as electroplating, circuit board manufacturing, film manufacturing, metal surface finishing, battery production and coal power plants. It is able to quickly react with various heavy metal ions in waste water at room temperature to form super macromolecule chelating ligands that are insoluble in water, have good chemical stability, and have large and dense flocs. The super macromolecule chelating ligands are separated by settling and filtering without complicated devices and procedures. The compound heavy metal chelating agent provided by the present invention has a wide application range, which is not only adapt to the heavy metal ions in the free state, but also the heavy metal ions in the complex state, and does not need to add a coagulant aid. In addition, it has good processing effect, is able to effectively treat low-concentration heavy metal wastewater, and the treated effluent is able to meet existing discharge standards.

Moreover, the compound heavy metal chelating agent provided by the present invention is also able to be used to treat various solid wastes containing heavy metal pollutants. The solid wastes are not particularly limited, as long as they are solid wastes containing heavy metals, such as fly ash, soil, sludge, waste residues and sediments.

DETAILED DESCRIPTION OF THE PREFERRED EMBODIMENT

The compound heavy metal chelating agent containing dithiocarboxylate functionalized ethoxylated pentaerythritol core hyperbranched polymer provided by the present invention will be described in detail with reference to embodiments as below, but these embodiments are unable to be understood as limiting the protective scope of the present invention.

First Embodiment

Preparation of dithiocarboxylate functionalized pentaerythritol core hyperbranched polymer and di sodium N,N'-bis-(dithiocarboxy) ethylenediamine compound heavy metal chelating agent:

Under nitrogen protection, add 36.00 g (0.60 mol) of ethylenediamine (EDA) and 36.00 g of methanol to a round-bottomed flask with a stirrer, a reflux condenser, a constant pressure dropping funnel and a thermometer, stir at 25° C.; and then add 52.80 g (0.10 mol) of ethoxylated pentaerythitol tetraacrylate (EPTA) and 52.80 g of methanol to the constant pressure dropping funnel to obtain an intermediate mixture, divide the intermediate mixture into three equal parts, add the three equal parts to the round-bottomed flask drop by drop in sequence every 6 hours; and then react for 28 h at 25° C., obtain a mixed methanol solution of ((N-(2-aminoalkylene))-3-aminopropionate) hyperbranched polymer and ethylenediamine; and then cool to 20° C., add 96.00 g (1.20 mol, 50%) of sodium hydroxide aqueous solution and 91.20 g (1.20 mol) of carbon disulfide drop by drop; and then react for 5 h at 25° C., precipitate a solid product, filter and dry under vacuum to obtain 188.22 g of a white product with a yield of 91.19%, namely, the compound heavy metal chelating agent containing dithiocarboxylate functionalized ethoxylated pentaerythritol core hyperbranched polymer (EPTA/EDA/DTC) and disodium N,N'-bis-(dithiocarboxy) ethylenediamine (EDA/DTC), wherein a molar ratio of the EPTA/EDA/DTC and the EDA/DTC is 1:2.

Chemical shifts of the characteristic absorption peak of $^{13}$C nuclear magnetic resonance spectrum ($D_2O$) of the white product are respectively: 34,23, 39.98, 41.19, 45.56, 46.92, 59.39, 66.01, 68.24, 69.03, 174.89, 210.76, 212.31 and 213.94 ppm, which shows that the compound heavy metal chelating agent is a mixture of dithiocarboxylate functionalized ethoxylated pentaerythritol core hyperbranched polymer (EPTA/EDA/DTC) and disodium N,N'-bis-(dithiocarboxy) ethylenediamine (EDA/DTC) with a structural formula of (V)

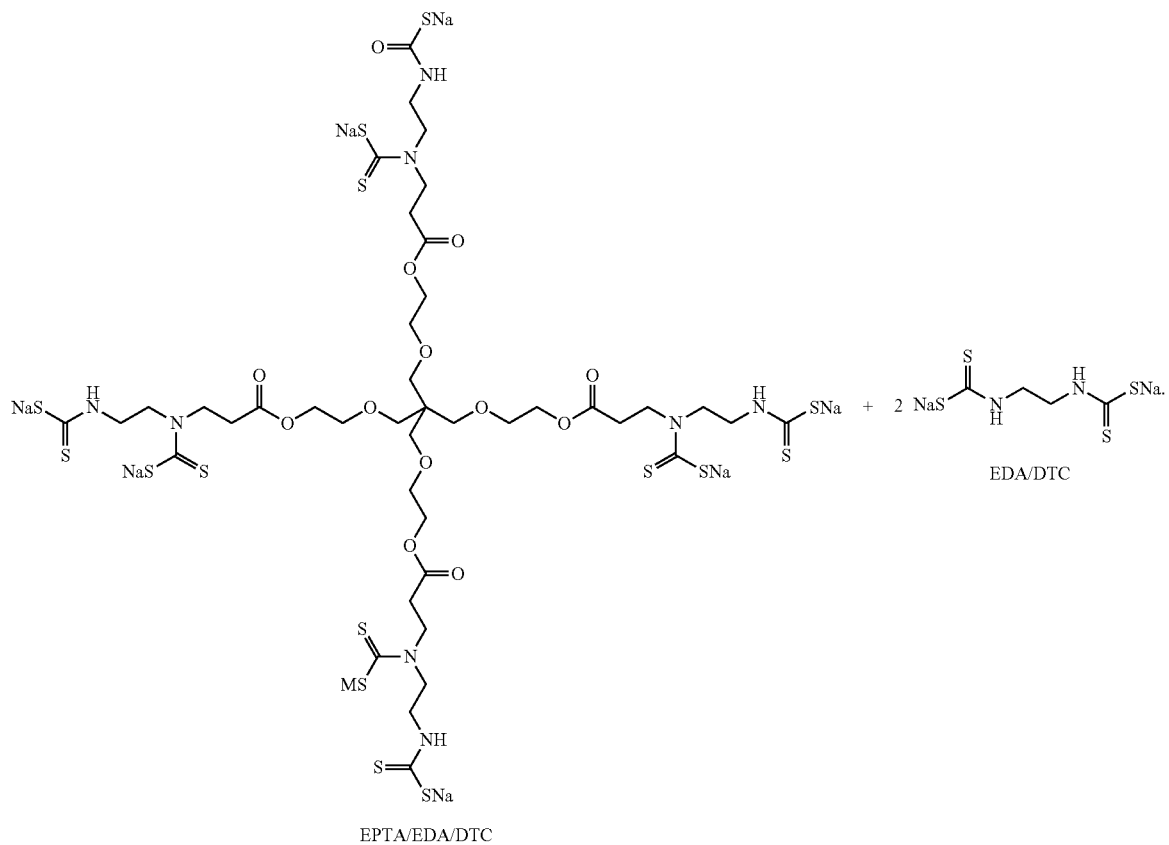

Second Embodiment

Preparation of dithiocarboxylate functionalized pentaerythritol core hyperbranched polymer and 1,4-butanediamine-N,N'-sodium bisdithiocarboxylate compound heavy metal chelating agent:

Under nitrogen protection, add 52.80 g (0.60 mol) of 1,4-butanediamine (BDA) and 52.80 g of ethanol to a round-bottomed flask with a stirrer, a reflux condenser, a constant pressure dropping funnel and a thermometer, stir at 25° C.; and then add 52.80 g (0.10 mol) of ethoxylated pentaerythitol tetraacrylate (EFTA) and 52.80 g of ethanol to the constant pressure dropping funnel to obtain an intermediate mixture, divide the intermediate mixture into three equal parts, add the three equal parts to the round-bottomed flask drop by drop in sequence every 6 hours; and then react for 28 h at 25° C., obtain a mixed ethanol solution of ((N-(4-aminoalkylene))-3-aminopropionate) hyperbranched polymer and 1,4-butanediamine; and then cool to 20° C., add 96.00 g (1.2.0 mol, 50%) of sodium hydroxide aqueous solution and 91.20 g (1.20 mol) of carbon disulfide drop by drop; and then react for 5 h at 25° C., precipitate a yellowish solid product, filter and dry under vacuum to obtain 209.18 g of a white product with a yield of 93.72%, namely, the compound heavy metal chelating agent containing dithiocarboxylate functionalized ethoxylated pentaerythritol core hyperbranched polymer (EPTA/BDA/DTC) and 1,4-butanediamine-N,N'-sodium bisdithiocarboxylate (BDA/DTC), wherein a molar ratio of the EPTA/BDA/DTC and the BDA/DTC is 1:2.

Chemical shifts of the characteristic absorption peak of $^{13}C$ nuclear magnetic resonance spectrum ($D_2O$) of the white product are respectively: 25.24, 26.98, 27.21, 31.26, 45.61, 45.98, 50.25, 53.24, 65.32, 68.38, 70.90, 47.03, 172.32, 211.98, 212.18 and 213.36 ppm, which shows that the compound heavy metal chelating agent is a mixture of dithiocarboxylate functionalized ethoxylated pentaerythitol core hyperbranched polymer (EPTA/BDA/DTC) and 1,4-butanediamine-N,N'-sodium bisdithiocarboxylate (BDA/DTC) with a structural formula of

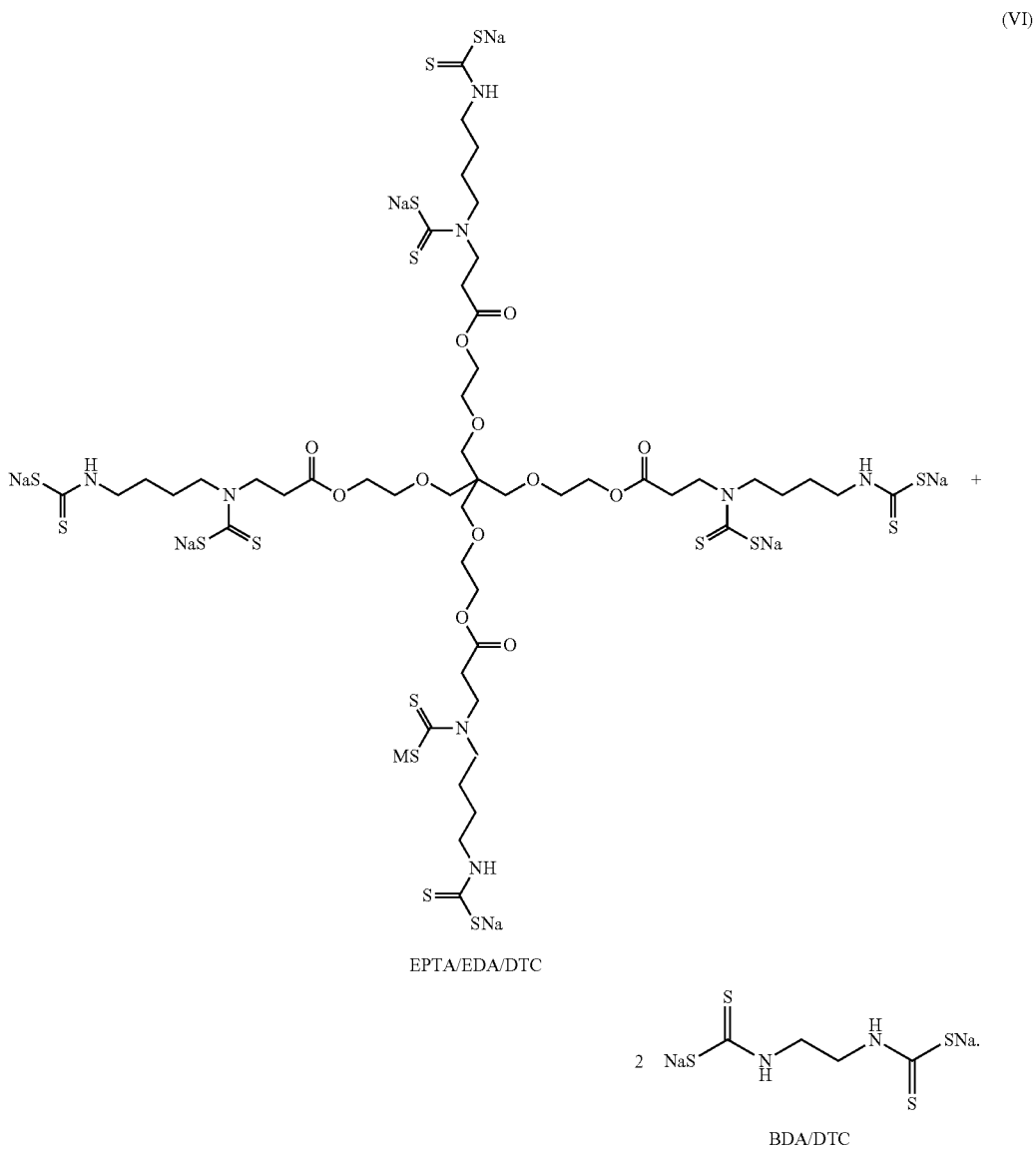

Third Embodiment

Preparation of dithiocarboxylate functionalized pentaerythritol core hyperbranched polymer and 1,6-hexanediamine-N,N'-sodium bisdithiocarboxylate compound heavy metal chelating agent:

Under nitrogen protection, add 81.20 g (0.70 mol) of 1,6-hexanediamine (HDA) and 81.20 g of ethanol to a round-bottomed flask with a stirrer, a reflux condenser, a constant pressure dropping funnel and a thermometer, stir at 20° C.; and then add 52.80 g (0.10 mol) of ethoxylated pentaerythitol tetraacrylate (EPTA) and 52.80 g of ethanol to the constant pressure dropping funnel to obtain an intermediate mixture, divide the intermediate mixture into two equal parts, add one of the two equal parts to the round-bottomed flask drop by drop, stir for 4 h, add another of the two equal parts drop by drop; and then react for 24 h at 25° C., obtain a mixed ethanol solution of ((N-(6-aminoalkylene))-3-aminopropionate) hyperbranched polymer and 1,6-hexanediamine; and then cool to 20° C., add 112.00 g (1.40 mol, 50%) of sodium hydroxide aqueous solution and 106.40 g (1.40 mol) of carbon disulfide drop by drop; and then react for 5 h at 25° C., precipitate a yellowish solid product, filter and dry under vacuum to obtain 244.26 g of a white product with a yield of 90.07%, namely, the compound heavy metal chelating agent containing dithiocarboxylate functionalized ethoxylated pentaerythritol core hyperbranched polymer and 1,6-hexanediamine-N,N'-sodium bisdithiocarboxylate with a molar ratio of 1:3.

Chemical shifts of the characteristic absorption peak of $^{13}C$ nuclear magnetic resonance spectrum ($D_2O$) of the white product are respectively: 25.68, 25.98, 26.42, 29.34, 29.93, 30.56, 33.74, 43.28, 48.28, 49.26, 50.28, 53.84, 67.94, 68.82, 71.06, 174.92, 211.16, 212.06 and 212.98 ppm, which shows that the compound heavy metal chelating agent is a mixture of dithiocarboxylate functionalized ethoxylated pentaerythritol core hyperbranched polymer and 1,6-hexanediamine-N,N'-sodium bisdithiocarboxylate with a structural formula of

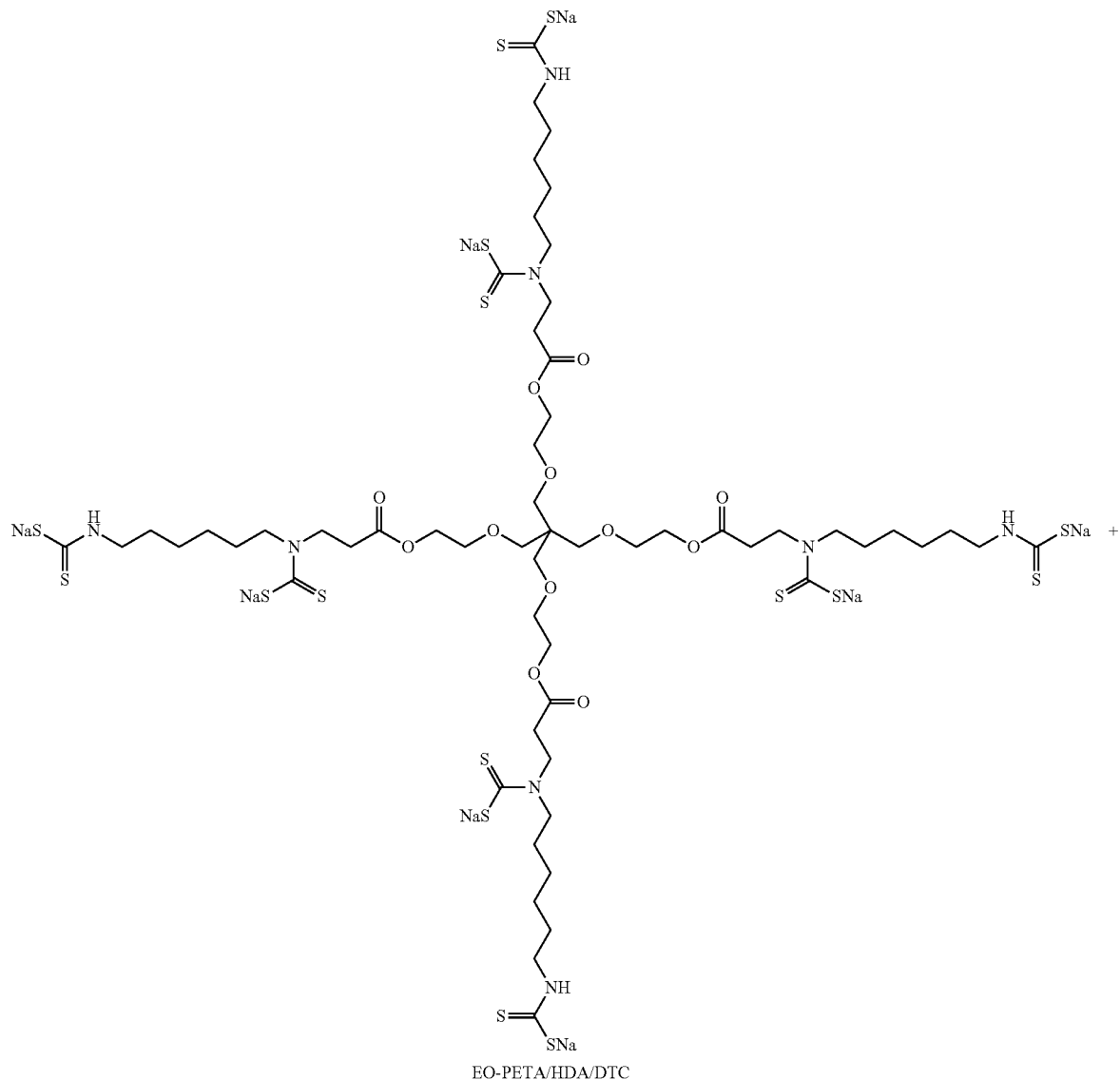

EO-PETA/HDA/DTC

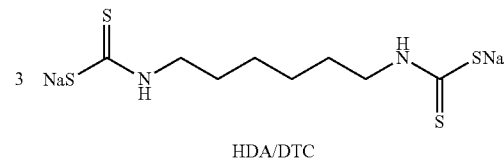

HDA/DTC

First Control Example

Commercially available sodium diethyldithiocarbamate solid

Second Control Example

Commercially available disodium N,N'-bis-(dithiocarbo-ethylenediamine

Fourth Embodiment

Treatment of copper-containing electroplating wastewater

The compound heavy metal chelating agents obtained by the first embodiment, the second embodiment and the third embodiment, and the traditional chelating agents provided by the first control example and the second control example are used to treat heavy metal wastewater (pH 3.7, $Cu^{2+}$ 16.12 $mg \cdot L^{-1}$ and $Ni^{2+}$ 5.68 $mg \cdot L_{-1}$) from a circuit board factory in Shanghai, China respectively.

A treatment method comprises steps of: (1) adjusting a pH value of the heavy metal wastewater to 7.0 with NaOH; (2) taking 500 mL of the heavy metal wastewater, stirring at 150 rpm for 10 min with a stirrer, simultaneously adding a chelating agent on a base of dry basis; (3) performing a next step for the compound heavy metal chelating agents provided by the first embodiment, the second embodiment and the third embodiment, or adding a polyacrylamide (PAM) aqueous solution with a mass concentration of 0.1% and a density of 50 $mg \cdot L^{-1}$ to the traditional chelating agents provided by the first control example and the second control example, stirring at 50 rpm for 5 min; and (4) standing for 30 min, filtering and determining a heavy metal content with ICP-MS (7700, Agilent). Determination results are shown in Table 1.

TABLE 1

Result comparison of treatment on heavy metal wastewater ($Cu^{2+}$ 16.12 $mg \cdot L^{-1}$)

| Chelating agent | Concentration ($mg \cdot L^{-1}$) | Whether PAM is added | Heavy metals in water ($mg \cdot L^{-1}$) $Cu^{2+}$ | Ni | Precipitation |
|---|---|---|---|---|---|
| First Embodiment | 120 | No | 1.09 | 0.98 | Large particles, dense, fast |
|  | 130 | No | 0.23 | 0.11 | settling, easy separation, |
|  | 140 | No | 0 | 0.07 | less sludge |
| Second Embodiment | 120 | No | 2.25 | 1.45 | Large particles, dense, fast |
|  | 130 | No | 0.18 | 0.09 | settling, easy separation, |
|  | 140 | No | 0 | 0.01 | less sludge |
| Third Embodiment | 120 | No | 2.34 | 1.25 | Large particles, dense, fast |
|  | 130 | No | 0.29 | 0.43 | settling, easy separation, |
|  | 140 | No | 0.06 | 0.08 | less sludge |
| First Control Example | 120 | Yes | 2.93 | 1.97 | Fine particles, slow settling, |
|  | 150 | Yes | 1.01 | 0.98 | need PAM for coagulation, |
|  | 200 | Yes | 1.02 | 0.98 | and large amount of sludge |
| Second Control Example | 120 | Yes | 1.61 | 1.73 | Small particles, slow |
|  | 130 | Yes | 0.48 | 1.28 | settling, need PAM to help |
|  | 150 | Yes | 0.27 | 1.29 | coagulation, and large |
|  | 200 | Yes | 0.373 | 0.12 | amount of sludge |
| Special heavy metal emission limit standards in Table 3 of "Emission Standards of Electroplating Pollutant (GB21900-2008)" |  |  | 0.3 | 0.1 | — |

It is able to be seen from Table 1 that the composite heavy metal chelating agents provided by the present invention has a good removal effect on $Cu^{2+}$, and the concentration of $Cu^{2+}$ after treatment is lower than special heavy metal emission limit standards in Table 3 of "Emission Standards of Electroplating Pollutant (GB21900-2008)". Judging from the morphology of the deposit formed by the compound heavy metal chelating agents with heavy metals, the floc deposits formed by the compound heavy metal chelating agents, which are provided by the first embodiment, the second embodiment and the third embodiment of the present invention, with the heavy metals are large and dense in particles, and have a fast settling speed, do not need PAM to help coagulation, so the sludge is less. However, the floc deposits, formed by sodium diethyldithiocarbamate of the first control example with heavy metals, are small in particles, have a slow settling speed, need PAM to help coagulation, so the sludge is much, which is unable to meet special heavy metal emission limit standards in Table 3 of "Emission Standards of Electroplating Pollutant (GB21900-2008) ". The floc deposits, formed by disodium N,N'-bis-(dithiocarboxy) ethylenediamine of the second control example with heavy metals, are small in particles, have a slow settling speed, need PAM to help coagulation, so the sludge is much, which is also unable to meet special heavy metal emission limit standards in Table 3 of "Emission Standards of Electroplating Pollutant (GB21900-2008)".

Fifth Embodiment

Treatment of mercury-containing wastewater

The compound heavy metal chelating agent obtained by the first embodiment, and the traditional chelating agents provided by the first control example and the second control example are used to treat blast furnace washing water (pH 1.65, $Hg^{2+}$ 1.566 mg·$L^{-1}$, $Ni^{2+}$ 0.828 mg·$L^{-1}$ and $Pb^{2+}$ 1.029 mg·$L^{-1}$) from an enterprise in Shanghai, China respectively.

A treatment method comprises steps of: (1) adjusting a pH value of the blast furnace washing water to 7.0 with NaOH; (2) taking 500 mL of the blast furnace washing water, stirring at 150 rpm for 10 min with a stirrer, simultaneously adding a chelating agent on a base of dry basis; (3) stirring at 50 rpm for 30 min; (4) standing for 30 min, filtering and determining a heavy metal content with ICP-MS (7700, Agilent), Determination results are shown in Table 2.

TABLE 2

Result comparison of treatment on blast furnace washing water

| Serial No. | Concentration (mg · $L^{-1}$) | Heavy metals in water (mg · $L^{-1}$) | | | Precipitation |
|---|---|---|---|---|---|
| | | $Hg^{2+}$ | $Ni^{2+}$ | $Pb^{2+}$ | |
| Raw water | | 1.566 | 0.828 | 1.029 | |
| First embodiment | 10 | 0.001 | 0.013 | 0.035 | Flocs are produced |
| Second embodiment | 10 | 0.001 | 0.011 | 0.033 | Flocs are produced |
| Third embodiment | 10 | 0.002 | 0.009 | 0.026 | Flocs are produced |
| First control example | 10 | 1.566 | 0.828 | 1.029 | No floc is produced |
| | 20 | 1.566 | 0.828 | 1.029 | |
| | 30 | 1.566 | 0.828 | 1.029 | |
| Second control example | 10 | 1.566 | 0.828 | 1.029 | No floc is produced |
| | 20 | 1.566 | 0.828 | 1.029 | |
| | 30 | 1.566 | 0.828 | 1.029 | |
| Shanghai Local Standard "Comprehensive Emission Standard DB31/199-2018" | | 0.005 | 0.1 | 0.1 | — |

The treatment of low-concentration heavy metal wastewater is an industry problem. It is able to be seen from Table 2 that the compound heavy metal chelating agents provided by the present invention has a good removal effect on low-concentration heavy metal wastewater. Because the heavy metal chelating agent containing hyperbranched polymer is synergized with the micromolecular disodium N,N'-bis-(dithiocarboxy) ethylenediamine, and alternately chelated with heavy metals to form larger chelate deposits, thereby producing macroscopic floc deposits, which is able to satisfy Shanghai Local Standard "Comprehensive Emission Standard DB31/199-2018" after filtration. However, the sodium diethyldithiocarbamate solid provided by the first control example, and the disodium N,N'-bis-(dithiocarboxy) ethylenediamine provided by the second control example are unable to produce floc deposits, and unable to effectively treat the low-concentration heavy metal wastewater.

It is able to be seen from the above embodiments that the hyperbranched polymer compound heavy metal chelating agent provided by the present invention has a wide application range while processing heavy metals, does not need to add coagulant, has a good processing effect, and has both chelation and flocculation functions. Therefore, it is able to effectively treat low-concentration wastewater.

The above are only the preferred embodiments of the present invention. It should be pointed out that for those skilled in the art, without departing from the principles of the present invention, several improvements and modifications are able to be made. These improvements and modifications should also be regarded as the protective scope of the present invention.

What is claimed is:

1. A compound heavy metal chelating agent, which comprises dithiocarboxylate functionalized ethoxylated pentaerythritol core hyperbranched polymer and alkylene diamine-N,N'-sodium bisdithiocarboxylate, wherein:
   the dithiocarboxylate functionalized ethoxylated pentaerythritol core hyperbranched polymer has a chemical formula of $C[CH_2OCH_2CH_2OCOCH_2CH_2N(CSSM)(CH_2)_n NHCSSM]_4$; the alkylene diamine-N,N'-sodium bisdithiocarboxylate has a chemical formula of $(MSSC)_2N(CH_2)_nN(CSSM)_2$, here n is a positive integer between 2 and 12, M is $Na^+$, $K^+$ or $NH_4^+$;
   a molar ratio of the dithiocarboxylate functionalized ethoxylated pentaerythritol core hyperbranched polymer and the alkylene diamine-N,N'-sodium bisdithiocarboxylate is in a range from 1:1.0 to 1:10.0.

2. A preparation method of a compound heavy metal chelating agent, wherein:
   the compound heavy metal chelating agent comprises dithiocarboxylate functionalized ethoxylated pentaerythritol core hyperbranched polymer and alkylene diamine-N,N'-sodium bisdithiocarboxylate, wherein:
      the dithiocarboxylate functionalized ethoxylated pentaerythritol core hyperbranched polymer has a chemical formula of $C[CH_2OCH_2CH_2OCOCH_2CH_2N(CSSM)(CH_2)_n NHCSSM]_4$;

the alkylene diamine-N,N'-sodium bisdithiocarboxylate has a chemical formula of $(MSSC)_2N(CH_2)_nN(CSSM)_2$, here n is a positive integer between 2 and 12, M is $Na^+$, $K^+$ or $NH_4^+$;

a molar ratio of the dithiocarboxylate functionalized ethoxylated pentaerythritol core hyperbranched polymer and the alkylene diamine-N,N'-sodium bisdithiocarboxylate is in a range from 1:1.0 to 1:10.0;

the preparation method comprises steps of:

(1) performing a first addition reaction, which comprises adding a first low-carbon alcohol solution drop by drop into a second low-carbon alcohol solution at 20-25° C. under nitrogen protection, wherein the first low-carbon alcohol solution contains ethoxylated pentaerythritol tetraacrylate (EPTA), the second low-carbon alcohol solution contains excessive alkylenediamine (ADA) with a chemical formula of $H_2N(CH_2)_n NH_2$, here n is a positive integer between 2 and 12; and then obtaining a mixed low-carbon alcohol solution which contains (N-(n-aminoalkylene))-3-aminopropionate hyperbranched polymer and unreacted alkylenediamine by stirring for 20-48 h at 20-35° C.; and (2) performing a second addition reaction, which comprises adding alkaline aqueous solution and carbon disulfide drop by drop after cooling the mixed low-carbon alcohol solution obtained by the step (1) to 10-25° C., stirring for 3-8 h at 20-35° C., standing at room temperature for 3-24 h, precipitating a solid product, filtering and drying to obtain the compound heavy metal chelating agent, wherein:

a molar ratio of the EPTA, the ADA, the alkali and the carbon disulfide is in a range of 1: (5.0-14.0): (10.0-28.0): (10.0-28.0).

3. The preparation method according to claim 2, wherein each of the first low-carbon alcohol and the second low-carbon alcohol in the step (1) is one member selected from the group consisting of methanol, ethanol, propanol, ethylene glycol and propylene glycol.

4. The preparation method according to claim 2, wherein the step (1) of performing the first addition reaction comprises adding the first low-carbon alcohol solution containing ethoxylated pentaerythritol tetraacrylate into the second low-carbon alcohol solution containing excessive alkylenediamine at 20-25° C. under nitrogen protection drop by drop, and then stirring for 4-8 h both of which are repeated for 1 to 10 times, and then obtaining the mixed low-carbon alcohol solution which contains N-(n-aminoalkylene))-3-aminopropionate hyperbranched polymer and unreacted alkylenediamine by stirring for 20-48 h at 20-35° C.

5. The preparation method according to claim 2, wherein the alkali in the step (2) is one member selected from the group consisting of sodium hydroxide, potassium hydroxide and ammonia.

6. A method for treating heavy metal wastewater comprising applying a compound heavy metal chelating agent wherein the compound heavy metal chelating agent comprises dithiocarboxylate functionalized ethoxylated pentaerythritol core hyperbranched polymer and alkylene diamine-N,N'-sodium bisdithiocarboxylate, wherein:

the dithiocarboxylate functionalized ethoxylated pentaerythritol core hyperbranched polymer has a chemical formula of $C[CH_2OCH_2CH_2OCOCH_2CH_2N(CSSM)(CH_2)_n NHCSSM]_4$;

the alkylene diamine-N,N'-sodium bisdithiocarboxylate has a chemical formula of $(MSSC)_2N(CH_2)_n N(CSSM)_2$, here n is a positive integer between 2 and 12, M is $Na^+$, $K^+$ or $NH_4^+$;

a molar ratio of the dithiocarboxylate functionalized ethoxylated pentaerythritol core hyperbranched polymer and the alkylene diamine-N,N'-sodium bisdithiocarboxylate is in a range from 1:1.0 to 1:10.0.

* * * * *